United States Patent [19]

Slifkin

[11] Patent Number: 4,942,126
[45] Date of Patent: Jul. 17, 1990

[54] METHOD OF EXTRACTING ANTIGENS OF BACTERIA

[75] Inventor: Malcolm Slifkin, Pittsburgh, Pa.

[73] Assignee: Allegheny-Singer Research Institute, Pittsburgh, Pa.

[21] Appl. No.: 896,053

[22] Filed: Aug. 13, 1986

[51] Int. Cl.$^5$ .............................................. G01N 33/53
[52] U.S. Cl. ......................................... 435/7; 435/24; 435/909; 436/547; 436/548
[58] Field of Search ............................. 435/24, 7, 909; 530/350; 436/501, 547, 548

[56] References Cited

PUBLICATIONS

Biological Abstract 83 (11): 108788.
Davis et al., Microbiology, 3rd Edition (1980), "*Vibrionaceal*", pp. 665–668.
Stanier et al., Microbial World, (1976), "*Campylobacter and Bdellovibrio*", p. 609.
Wong et al., Journal of Clinical Microbiology, vol. 21, No. 5, pp. 702–707, May 1985.
McCarthy, L. in Rapid Detection and Identification of Infectious Agents, Kingsbury et al. (ed), pp. 165–175, 1985.
Garcia et al., Diagnostic Parasitology Clinical Laboratory Manual, pp. 12–18, 1979.
Buck et al., Journal of Clinical Microbiology, vol. 29, No. 6, pp. 1094–1098, Dec. 1984.
Martinez et al., Journal of Bacteriology, vol. 109, No. 3, pp. 1239–1246, Mar. 1972.
Lior et al., Journal of Clinical Microbiology, vol. 15, No. 5, pp. 761–768, May 1982.
Penner et al., Journal of Clinical Microbiology, vol. 12, No. 6, pp. 732–737, Dec. 1980.
Logan et al., Journal of Bacteriology, vol. 168, No. 2, pp. 739–745, Nov. 1986.
Wenman et al., Journal of Clinical Microbiology, vol. 21, No. 1, pp. 108–112, Jan. 1985.
Sigma Chemical Company Catalog, pp. 770–771, Feb. 1984.

Primary Examiner—Esther M. Kepplinger
Assistant Examiner—Carol A. Spiegel
Attorney, Agent, or Firm—Webb, Burden, Ziesenheim & Webb

[57] ABSTRACT

A means for identifying *C. jejuni*, from stool specimens, by the extraction and agglutination of its soluble antigen(s). More specifically, bacteria are concentrated from fresh (unpreserved) stool specimens, soluble antigen is released—preferably either by a specified heating protocol or by the action of a particular enzyme—and the antigen is detected by agglutination upon exposure to monoclonal, polyclonal or other corresponding antibodies. The method of the invention not only fosters efficiency in the laboratory but also provides rapid diagnosis of the presence of *C. jejuni*, so that appropriate patient treatment may begin at the earliest opportunity.

9 Claims, No Drawings

4,942,126

METHOD OF EXTRACTING ANTIGENS OF BACTERIA

FIELD OF THE INVENTION

The present invention relates to the identification, by their enzyme- or heat-soluble antigens, of pathogenic bacteria in feces, which bacteria are causal of enteritis and related diseases in humans.

INTRODUCTION

Effective treatment of nonviral diarrheal illness (enteritis, dysentary, etc.) ordinarily requires accurate identification of the causal bacterial pathogen. Although the best known enteritis-causing bacteria include the Salmonella and Shigella species, the role of *Campylobacter jejuni* (*C. jejuni*) in human enteritis has recently been recognized as well. Indeed, the organism has been found in 3 to 11 percent of patients with diarrheal illness in Europe and North America. Moreover, it has been isolated in virtually every country, whether temperate or tropical, in which it has been sought. Fecal specimens from patients with diarrhea should therefore be examined routinely for the presence of *C. jejuni*, in addition to the other diagnostic tests which are already routinely performed.

*C. jejuni* is microaerophilic and requires a special environment for successful incubation. The routine methods of stool culturing for this reason ordinarily fail to isolate *C. jejuni* because, under conditions adverse to its growth, the organism is quickly overgrown by the predominant enteric flora. Laboratory identification of *C. jejuni* has therefore ordinarily required separate culturing with special culture media and elevated temperatures, along with a total incubation time of 48 to 72 hours.

As a result, in order to effect rapid diagnosis and treatment, a need remains for a method that will identify *C. jejuni* from stool specimens in a relatively short period of time, without culturing, and with a minimum of attention by the laboratory or other health care personnel.

BRIEF DESCRIPTION OF THE INVENTION

In order to meet this need, the present invention is a means for identifying *C. jejuni*, from stool specimens, by the extraction and agglutination of its soluble antigen(s). More specifically, bacteria are concentrated from stool specimens, soluble antigen is released—preferably either by a specified heating protocol or by the action of a particular enzyme—and the antigen is detected by agglutination upon exposure to monoclonal, polyclonal or other corresponding antibodies. The method of the invention not only fosters efficiency in the laboratory but also provides rapid diagnosis of the presence of *C. jejuni* without culturing, so that appropriate patient treatment may begin at the earliest opportunity.

DETAILED DESCRIPTION OF THE INVENTION

Recent investigations have been pursued on the serotypes of Campylobacter specimens with autoclaved, boiled or formalized antigen preparations. There have been no investigations to date, however, which report the use of soluble antigenic extracts for the detection of the antigens of *C. jejuni*, from either pure culture or from mixed culture of bacteria associated with this organism. Accordingly, the present invention provides a direct identification technique for use with extracted bacteria found in fecal specimens.

The present method is therefore a simple diagnostic test, which may be performed on fecal specimens (usually human fecal specimens), in order to confirm or negate a suspected presence of *C. jejuni* therein. Confirmation is achieved by the agglutination of a soluble antigen by a latex agglutination or coagglutination test as well as other agglutination tests. As described in detail below, the test may be completed within 30 minutes and includes the three main phases of concentration, extraction, and agglutination.

CONCENTRATION

Concentration of *C. jejuni* from a stool specimen commences with homogenization of an aliquot of the specimen. Watery stool specimens ordinarily need little or no agitation to form a homogeneous suspension; for example, a tube or vial containing the aliquot need only be sharply snapped with the fingers three or four times. If the stool is formed, a few ml. of physiological saline or buffer or a bacteriological broth (all well known in the art) is mixed into the stool sample in order to yield an emulsified-liquid aliquot. In either case, the suspension need have no specific concentration or viscosity but need have only the appearance of a roughly homogeneous aqueous suspension.

After the feces homogenizate is prepared, the *C. jejuni* in the aliquot may be concentrated by the preferred technique of sucrose gradient differential centrifugation. To carry out this preferred technique, 3-5 mls. of 50 percent aqueous sucrose solution is pipetted into a centrifuge tube, and about 1-2 mls. of 25 percent aqueous sucrose solution is then pipetted on top of the 50 percent sucrose solution. A 1 ml. (approximately) aliquot of the fecal suspension is then pipetted atop the 25 percent sucrose solution. The tube is then centrifuged in a tabletop centrifuge at about 3000 RPM for 15 minutes at room temperature. A band of bacteria, which includes any *C. jejuni* present along with other fecal flora, will result at the interface of the two sucrose solutions. The band of bacteria is removed with a Pasteur pipette or other appropriate pipette and is subjected to one of the extraction technique outlined in the next section.

An alternate technique for bacterial concentration is the technique of Percoll gradient different centrifugation. Percoll (Pharmacia Fine Chemicals, Uppsala, Sweden) is a differential centrifugation medium which has a density of 1.131 g/ml. 3-5 ml. of 50 percent aqueous Percoll is added to a centrifuge tube, and approximately 1 ml. of feces suspension is pipetted atop the Percoll. The tube is then centrifuged in a tabletop centrifuge at 200×g at room temperature for about 15 minutes. The bacterial layer which contains the *C. jejuni* sediments within the center of the Percoll solution at a specific density of 1.19 g/ml. Some fine fecal particulates may also be present in the bacterial layer, but most of the nonbacterial fecal matter precipitates to the bottom of the centrifuge tube.

It is conceivable that one skilled in the art might identify other concentration techniques, for *C. jejuni*, with a minimum of experimentation. Unfortunately, applicant has already established that a 10–100 fold loss of organisms occurs with other concentration techniques such as Millipore filtration, etc. The present techniques described above, however, provide bacterial bands which maximize concentration of *C. jejuni* while minimizing the presence of unwanted fecal material in the concentrate. This maximized concentration of *C. jejuni* in turn contributes to maximized reliability in the results of the present method; the greater the C. jejuni concentration, the more likely a positive identification of the species will be.

EXTRACTION

Once concentrated, the presence of *C. jejuni* in a band of fecal bacteria may be confirmed by the extraction and identification of one or more soluble antigens. One of the two preferred extraction methods is the heat extraction method which follows. About 0.5 to 1 ml. of the bacteria band (derived in the previous section) is placed in a glass vial such as a centrifuge or test tube or other glass vial. The bacterial suspension is heated to 60° to 80° C. in a hot block, incubator or other heating unit adapted to receive a test vial and to hold it without contamination. Heating time is ordinarily 5 minutes or less. Antigen extraction is complete once the bacterial band reaches the 60° to 80° C. temperature, although the bacterial specimen may subsequently be allowed to cool if desired.

The second preferred extraction method is the subtilopeptidase extraction method. Subtilopeptidase, or *Bacillus subtilis* alkaline proteinase, is acquired or prepared by means known in the art. As with the heat extraction technique, about 0.5 to 1 ml. of the bacteria band (of the previous section) is placed in a glass vial. Instead of heating the vial, however, approximately 1 to 4 ml. of a 0.1 mg./ml. aqueous solution of subtilopeptidase is added to the vial. The vial is left undisturbed for approximately 5 to 10 minutes, after which extraction is complete.

Applicant believes that the above two extraction techniques provide for maximum antigen extraction, and thus maximum sensitivity and reliability in the text method of the present invention. As a result, although other extractions such as with comparable amounts of the enzymes trypsin, papain and pepsin appear to demonstrate effectiveness in most or all extractions, the above-described methods are preferred.

AGGLUTINATION

*C. jejuni* antisera is prepared as follows. Confluent bacterial growth on four Campy-blood agar plates (Remel Labs, Lenexa, Kans.) is obtained after 48 hours at 42° C. in a gas generator chamber "Bio Bag," Type CFJ, Marion Scientific, Kansas City, Mo. The bacteria are transferred by way of a flame-sterilized wire loop to 3 ml. of saline (0.85 percent NaCl). Six rabbits (preferably white New Zealand males) are then immunized intramuscularly with formalin-treated Campylobacter suspensions in complete Freund adjuvant. These animals are boosted one month later with a series of intravenous injections of the same bacterial suspensions in saline. Blood is obtained by cardiac puncture or via ear vein 1–10 days after the last injection and is allowed to clot. Sera is then collected and stored at −20° C.

Alternately, a monoclonal or polyclonal antibody of *C. jejuni* may be prepared by heating a *C. jejuni* suspension in phosphate buffer to 80° C. for 15 minutes. The filtered solution (0.45 $\mu$ filter) is used as the bacterial vaccine for the induction of a polyclonal or monoclonal antibody preparation by means known in the art.

A drop of the antigen-extracted bacterial suspension is placed on a glass microscope slide. A drop of the antisera described above (or, generally, an agglutination or coagglutination reagent prepared with polyclonal, monoclonal or other *C. jejuni*-specific antibody) is mixed with the drop of bacterial suspension by, for example, deposition of a drop of antisera onto the drop of antigen-extracted bacterial suspension and subsequently rocking the slide. The presence of extracted *C. jejuni* is indicated by an agglutination reaction that occurs within the following two minutes. The reaction may be observed, with the naked eye, by transillumination of the slide. Microscope observation or dot-ELISA agglutination detection may be used if the necessary equipment is readily available, but one of the advantages of the present invention is that the simple method may be accomplished quickly with very basic laboratory equipment i.e., vials, pipettes, glass slides and a tabletop centrifuge. Ambient light will in many cases be sufficient for transillumination of the slide.

If use of the dot-ELISA is desired, however, the following protocol may be considered exemplary. Extracted bacterial aliquots are "dotted" onto nitrocellulose membranes, and the dots are allowed to dry. The membranes are then blocked with 75 microliter of 10 percent bovine serum albumin for 1 hour. After the blocking solution is decanted, 50 percent of *C. jejuni* antisera (diluted in 1 percent gelatin in phosphate buffered saline) is added to each dot. After an hour's incubation at room temperature, the membrane is rinsed with water and washed three times with phosphate buffered saline. Consecutive additions of antisera may be completed in the same fashion if desired. Coloration and examination then proceed by means known in the art.

One embodiment of the invention may be conducted in accordance with the following examples.

EXAMPLE 1

Six New Zealand white male rabbits were immunized intramuscularly with formalin-treated Campylobacter suspensions in complete Freund adjuvant. A series of 3 booster inoculations was given one month later over a period of three days. Five days after the last injection, blood was drawn from ear veins in each rabbit. No attempt was made at exsanguination and no rabbit was sacrificed; all animals recovered. Sera separated from clotted blood was stored at −20° C.

EXAMPLE 2

A conical base centrifuge tube was filled with four ml. of 50% percent aqueous sucrose solution. One ml. of 25 percent aqueous sucrose solution was then placed atop the 50% sucrose solution and a 1 ml. aliquot of homogenized watery stool specimen (from a patient with symptomatic enteritis) was added atop the 25 percent sucrose solution. The tube was centrifuged in a tabletop centrifuge at about 3000 RPM for 15 minutes at room temperature.

A *C. jejuni*-containing bacterial layer appeared at the interface of the two sucrose solutions. One ml. of the bacterial band was removed with a pipette and was transferred to a glass test tube. The bacterial aliquot was heated to 70° C. over a 4 minute period in a laboratory hot block. One drop of the heated bacterial aliquot was placed on a glass microscope slide. A drop of the antisera prepared in Example 1 was dropped atop the bacterial drop, and the slide was rocked. A visible agglutination reaction, which occurred one minute after the two drops were mixed, confirmed the presence of *C. jejuni* in the fecal specimen.

Having described presently preferred embodiments of the invention, it is to be understood that they may be otherwise embodied within the scope of the appended claims. For example, although the primary contemplated use of the present method is in the extraction and detection of antigens of *C. jejuni*, over time as the bacterial populations mutate and evolve the present method will undoubtedly have equal applicability to the identification of other Campylobacter species which have similar soluble antigens.

I claim:

1. A method of identifying the presence of Campylobacter species in fecal specimens, comprising:
   (a) concentrating Campylobacter organisms from fecal specimens using a concentrating media having at least two layers of different densities to segregate the Campylobacter organisms between the layers;
   (b) extracting soluble antigens from said Campylobacter organisms; and
   (c) reacting said antigens with Campylobacter antisera to yield a detectable agglutinate.

2. The method according to claim 1, wherein the concentrating media comprise sucrose gradient media, wherein said sucrose gradient media contains at least two layers in which the sucrose concentrations differ.

3. The method according to claim 1, wherein the concentrating media comprise sucrose gradient medium having two layers, one layer comprising a 50% aqueous sucrose solution beneath a 25% aqueous sucrose solution; and, the extracting of solution antigens from said Campylobacter organisms is accomplished by heating said Campylobacter organisms.

4. The method according to claim 1, wherein the extracting of soluble antigens from said Campylobacter organisms is accomplished by heating said Campylobacter organisms to between 60° and 80° C.

5. The method according to claim 1, wherein the extracting of soluble antigens from said Campylobacter organisms is accomplished with an enzyme.

6. The method according to claim 1, wherein the extracting of soluble antigens from said Campylobacter organisms is accomplished with subtilopeptidase.

7. The method according to claim 1, wherein the reacting of said antigens and Campylobacter antisera is on a microscope slide to yield a visible agglutinate.

8. The method according to claim 7, wherein the reacting of said antigens and Campylobacter antisera is on a microscope slide with rocking of said slide to yield a visible agglutinate.

9. The method according to claim 8, wherein the reacting in step (c) yields a visible agglutinate within two minutes.

* * * * *

UNITED STATES PATENT AND TRADEMARK OFFICE
CERTIFICATE OF CORRECTION

PATENT NO. : 4,942,126
DATED : July 17, 1990
INVENTOR(S) : Malcolm Slifkin

It is certified that error appears in the above-identified patent and that said Letters Patent is hereby corrected as shown below:

Column 2 Line 45 "technique" should read --techniques--.

Column 2 Line 47 "different" should read --differential--.

Column 3 Line 37 "text" should read --test--.

Claim 3 Line 5 Column 6 "solution" should read --soluble--.

Signed and Sealed this

Twenty-fifth Day of February, 1992

Attest:

HARRY F. MANBECK, JR.

*Attesting Officer*  *Commissioner of Patents and Trademarks*